US00PP28901P2

(12) United States Plant Patent
Olesen

(10) Patent No.: US PP28,901 P2
(45) Date of Patent: Jan. 30, 2018

(54) COMPACT FLORIBUNDA ROSE PLANT NAMED 'POULPAL070'

(50) Latin Name: ***Rosa* hybrid**
Varietal Denomination: Poulpal070

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/330,302

(22) Filed: Sep. 6, 2016

(51) Int. Cl.
*A01H 5/02* (2006.01)

(52) U.S. Cl.
USPC ..... Plt./150

(58) Field of Classification Search
USPC ..... Plt./150
See application file for complete search history.

*Primary Examiner* — Annette Para

(57) ABSTRACT

A new garden rose plant of the compact floribunda class which has abundant, medium red flowers and attractive foliage. This new and distinct variety has shown to be uniform and stable in the resulting generations from asexual propagation.

2 Drawing Sheets

Botanical designation: *Rosa* hybrid.
Variety denomination: 'Poulpal070'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2009 and the resulting seeds were planted in a controlled environment in Fredensborg, Denmark. The new variety, named 'Poulpal070', originated as a single seedling from the stated cross.

The new variety may be distinguished from its male pollen parent and female seed parent primarily by the following characteristics. The male pollen parent plant has near white flowers, while the new variety has medium red flowers. The female seed parent plant has orange red flowers, while the new variety has medium red flowers.

The objective of the hybridization of this rose variety was to create a new and distinct variety for garden use with unique qualities, such as:

1. Uniform and abundant medium red flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpal070' from all other varieties of which we are aware.

As part of the rose development program, Mogens N. Olesen germinated the seeds from the aforementioned hybridization during winter of 2009 and conducted evaluations on the resulting seedlings in a controlled environment in Fredensborg, Denmark. 'Poulpal070' was selected in the spring of 2010 by the inventor as a single plant from the progeny of the aforementioned hybridization.

Asexual reproduction of 'Poulpal070' by traditional budding and rooted cuttings was first done by Mogens N. Olesen in the nursery in Fredensborg, Denmark in July, 2010. This initial and other subsequent asexual propagations conducted in controlled environments have demonstrated that the characteristics of 'Poulpal070' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal070'.

Specifically illustrated in FIG. 1 are juvenile and mature leaves, bare stem, flower petals detached, sepals detached showing reproductive flower parts and receptacle, and open flowers viewed above and side.

DETAILED DESCRIPTION OF THE VARIETY

Figure 1:
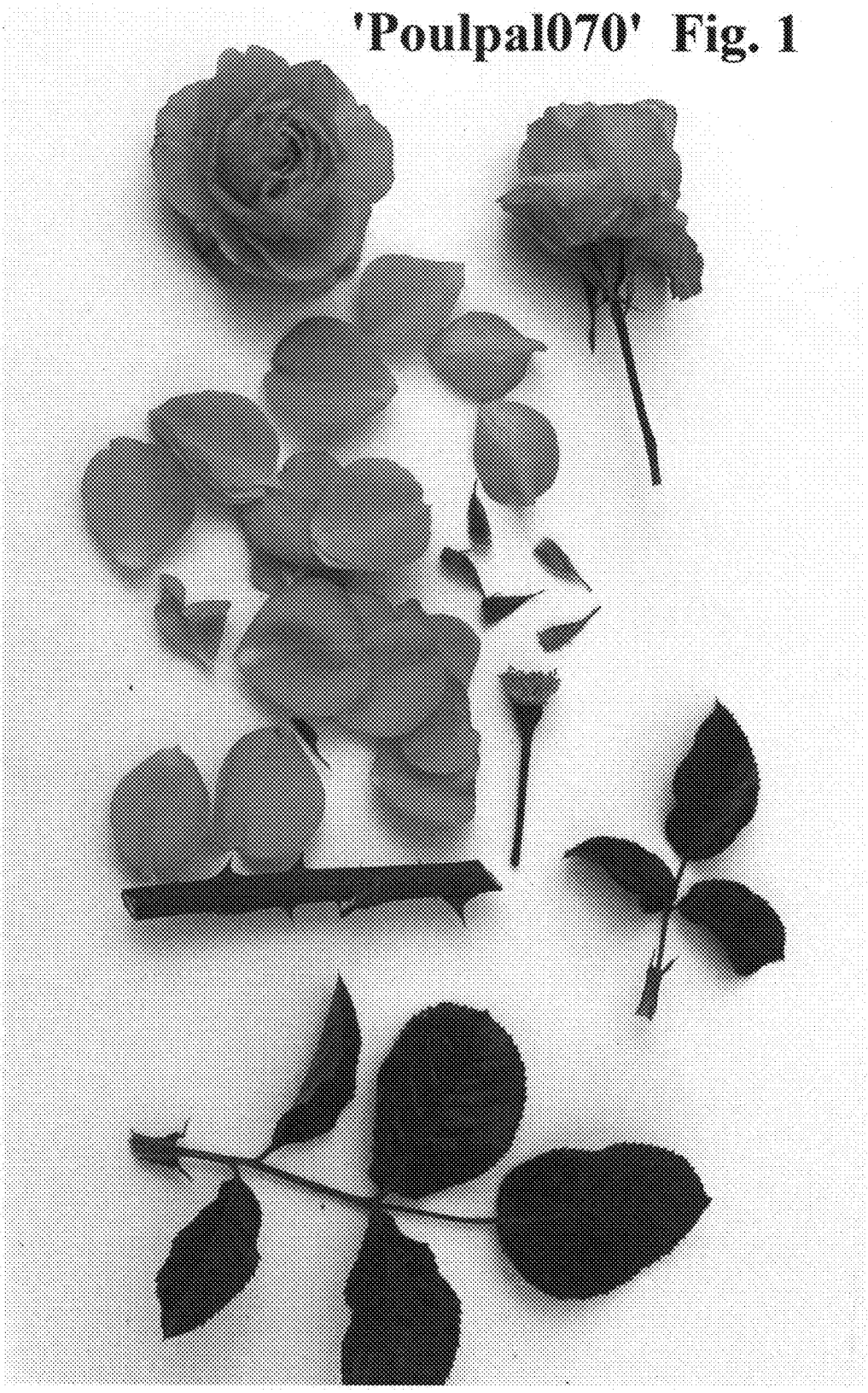
Figure 2:
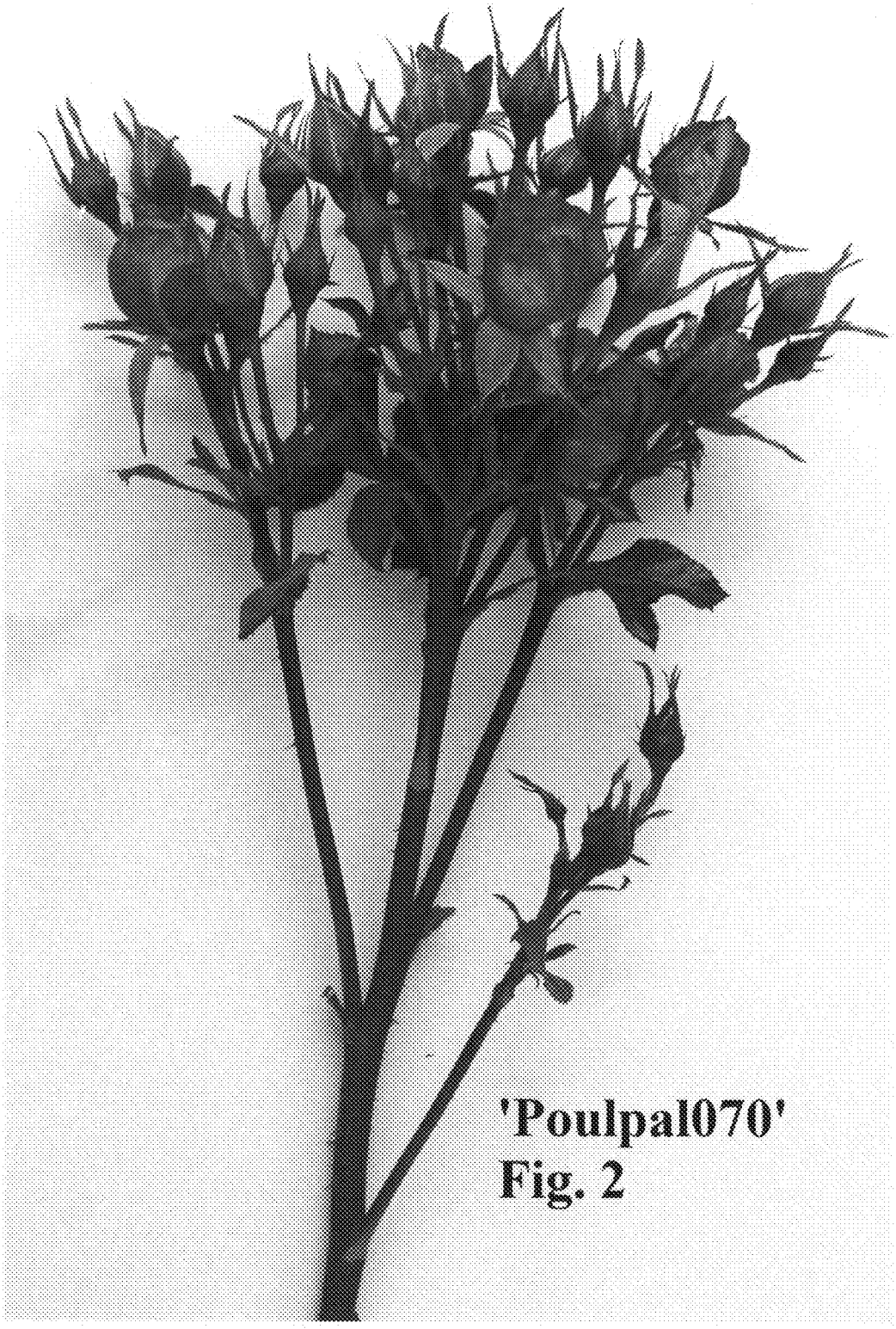
FIG. 2 shows a flowering branch with many flower buds upon opening. Plants shown are 2 years of age.

The following is a description of 'Poulpal070', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulcas031', U.S. Plant Pat. No. 22,502 are compared to 'Poulpal070' in Chart 1.

CHART 1

| | 'Poulpa1070' | 'Poulcas031' |
|---|---|---|
| Petal Count | 40 | 40 to 50 |
| Flower Diameter | 85 mm | 70 to 80 mm |
| General Tonality of Flower Color | Red Group 52A | Red-Purple Group N 57A |

Flower and Flower Bud

Blooming habit: Continuous.

Flower bud:

*Size*.—Upon opening, 27 mm in length from base of receptacle to end of bud. Bud diameter is 17 mm.

*Bud form*.—Ovoid.

*Bud color*.—As sepals divide petals are Red Group 46C.

*Sepal inner surface*.—Color: Yellow-Green Group and Greyed-Red Group 178C. Surface: Lightly pubescent.

*Sepal outer surface*.—Color: Yellow-Green Group 144A with intonations of Greyed-Red Group 179A. Texture: Smooth.

*Sepal shape*.—Apex: Cirrhose. Base: Flat at union with receptacle.

*Sepal margin*.—Many stipitate glands, strong foliaceous appendages on three of the five sepals.

*Sepal size*.—About 40 to 45 mm long, 10 mm wide.

*Receptacle*.—Texture: Smooth. Size: 5 mm in height, 10 mm wide. Color: Yellow-Green Group 144A with intonations of Greyed-Purple Group 185A. Shape: Campanulate.

*Pedicel*.—Surface: Smooth. Length: About 50 mm. Diameter: 4 mm on average. Color: Greyed-Purple Group 183A with intonations of Yellow-Green Group N144A. Strength: Moderate.

*Peduncle*.—Length: About 3 to 10 cm. Diameter: About 5 mm. Color: Greyed-Purple Group 183A with intonations of Yellow-Green Group 144A. Texture: Small prickles.

Flower bud development: Flower buds are borne in corymbs of about 5 flower buds found on each peduncle.

Flower bloom:

*Fragrance*.—Light rose scent.

*Duration*.—The blooms have a duration on the plant of approximately 10 days. Petals fall cleanly away from plant after flowers have fully matured.

*Size*.—Flower diameter is about 85 mm when open. Flower depth is about 45 mm.

*Flower shape*.—High centered, double, with a high pointed center which is tightly closed.

*Shape of flower, side view*.—The upper portion is flat. The lower portion is slightly concave.

Petalage: Under normal conditions, flowers have 40 petals.

General tonality of flower: Open flowers are Red Group 52A.

Petal color:

*Upon and after opening, outer and inner petals*.—Upper surface: Red Group 52B. Intonations of Red Group 41C at basal zone. Lower surface: Red Group 54A. Basal petal spots: Upper surface is Yellow Group 4A. Lower surface Yellow Group 4D.

Petals:

*Petal reflex*.—Flat.

*Margin*.—Entire and uniform, occasional cleft. Slight undulations.

*Shape*.—Generally rounded. Apex shape: Rounded. Base shape: Acute.

*Size*.—Up to 45 mm (l)×45 mm (w).

*Texture*.—Smooth.

*Thickness*.—Average.

Petaloids: None.

Reproductive flower parts:

*Pollen*.—None observed.

*Anthers*.—Size: 1 to 2 mm in length. Color: Greyed-Orange Group 167A. Quantity: 45 on average.

*Filaments*.—Color: Yellow Group 9A and Orange Group 25A towards the apex. Length: 9 mm.

*Pistils*.—Length: 7 mm. Quantity: 35 on average.

*Stigmas*.—Color: Yellow White Group 158A.

*Styles*.—Color: Red Group 46C.

*Location of stigmas*.—Level in location relative to the length of the filaments and the height of the anthers.

*Hips*.—None Observed.

Plant

Plant growth: Upright, bushy. Plants are 70 cm in height, and 60 cm wide.

Stems:

*Color*.—Juvenile growth: Yellow-Green Group 144A with intonations of Greyed-Purple Group 183B. Mature growth: Yellow-Green Group 144A with intonations of Greyed-Purple Group 183B.

*Length*.—On average, canes are 25 cm from the base of the plant to the flowering portion.

*Diameter*.—9 to 12 mm.

*Internodes*.—On mature canes about 40 mm between nodes.

*Surface texture*.—Young wood: Small prickles. Older wood: Small prickles.

Long prickles:

*Incidence*.—10 prickles per 10 cm of stem.

*Size*.—Average length of prickles on mature stems is 9 mm.

*Shape*.—Upper portion is linear. Lower portion is concave.

*Color*.—Juvenile prickles: Greyed-Purple Group 184A. Mature prickles: Greyed-Purple Group 184A.

Plant foliage:

*Compound leaf*.—175 mm (l)×130 (w).

*Quantity*.—2 leaves per 10 cm of stem on average.

*Leaf bearing angle to the stem*.—45 degrees.

*Color of juvenile foliage*.—Upper side: Yellow-Green Group 144A with intonations of Greyed-Purple Group 187A. Lower side: Yellow-Green Group 144B with intonations of Greyed-Purple Group 183A.

*Color of mature foliage*.—Upper side: Yellow-Green Group 147A. Lower side: Yellow-Green Group 146B.

Plant leaves and leaflets:

*Stipules*.—Size: 22 mm long, 4 mm wide. Quantity: 2 per compound leaf. Shape: Linear, slightly broad based with outward extending apices. Margins: Finely serrated. Color: Yellow-Green Group 144A.

*Petiole*.—Length: 30 mm. Diameter: 2 mm.

*Upper surface*.—Color: Yellow-Green Group 144A with intonations of Greyed-Red Group 178C.

*Lower surface*.—Color: Yellow-Green Group 144A.

*Rachis*.—Length: About 85 mm. Upper surface: Color: Yellow-Green Group 144A. Lower surface: Color: Yellow-Green Group 144A.

*Leaflet*.—Quantity: Normally 5 leaflets. Margins: Serrated. Size: On average terminal leaflets are 70 mm long, 55 mm wide. Shape: Generally elliptical. Base: Rounded. Apex: Slightly cuspidate. Texture:

Smooth. Thickness: Average. Arrangement: Odd pinnate. Venation: Reticulate. Glossiness: Glossy.

Disease resistance: Above average resistance to powdery mildew *Sphaerotheca pannosa*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the compact floribunda rose class named 'Poulpal070', substantially as illustrated and described herein, due to its abundant medium red flowers, disease resistance, and extended period of bloom.

* * * * *

'Poulpal070' Fig. 1

'Poulpal070'